US011980470B2

(12) United States Patent
Chiang

(10) Patent No.: US 11,980,470 B2
(45) Date of Patent: May 14, 2024

(54) EEG SIGNAL MONITORING ADAPTER DEVICE CONFIGURABLE ON EYEWEAR

(71) Applicant: Hsin-Yin Chiang, Strasbourg (FR)

(72) Inventor: Hsin-Yin Chiang, Strasbourg (FR)

(73) Assignee: CEPHALGO SAS, Strasbourg (FR)

( * ) Notice: Subject to any disclaimer, the term of this patent is extended or adjusted under 35 U.S.C. 154(b) by 712 days.

(21) Appl. No.: 17/138,964

(22) Filed: Dec. 31, 2020

(65) Prior Publication Data
US 2021/0121115 A1 Apr. 29, 2021
US 2024/0032839 A9 Feb. 1, 2024

Related U.S. Application Data

(60) Provisional application No. 63/028,632, filed on May 22, 2020.

(51) Int. Cl.
| | |
|---|---|
| *A61B 5/291* | (2021.01) |
| *A61B 5/00* | (2006.01) |
| *A61B 5/31* | (2021.01) |
| *A61B 5/384* | (2021.01) |
| *G02C 5/00* | (2006.01) |
| *G02C 5/14* | (2006.01) |
| *G02C 11/00* | (2006.01) |

(52) U.S. Cl.
CPC ............ *A61B 5/291* (2021.01); *A61B 5/0006* (2013.01); *A61B 5/31* (2021.01); *A61B 5/384* (2021.01); *A61B 5/6803* (2013.01); *A61B 5/7225* (2013.01); *G02C 5/001* (2013.01); *G02C 5/14* (2013.01); *G02C 11/10* (2013.01); *A61B 2562/222* (2013.01)

(58) Field of Classification Search
CPC .................................. G02C 5/14; G02C 5/001
USPC ......................................................... 351/123
See application file for complete search history.

(56) References Cited

U.S. PATENT DOCUMENTS

2021/0113139 A1* 4/2021 Hiratsuka .............. A61B 5/378
2021/0181844 A1* 6/2021 Paik ......................... A61B 5/38

FOREIGN PATENT DOCUMENTS

| CN | 106974646 A | * | 7/2017 |
| WO | WO-2017125081 A1 | * | 7/2017 |

* cited by examiner

*Primary Examiner* — Daniel J Colilla

(57) ABSTRACT

Presented is an EEG adapter device for eyewear which can be worn invisibly and continuously by the user. The eyewear adapter includes a main body configured in the form of a sleeve so that an intended temple of the eyewear can slidably fit therein, a ring configured to fit over the eyewear's temple and operable by a user to move a first EEG electrode of the eyewear adapter toward or away from the main body to ensure the first EEG electrode is adjustably positioned at FT9/FT10 of the 10-10 system. The eyewear adapter further includes a second EEG electrode and positioned in the vicinity of a bony region behind the user's ears, a third EEG electrode positioned at T9/T10 position of the 10-10 system when in use, and an electronics unit configured to receive and process EEG-related data from the first, the second, and the third EEG electrodes.

23 Claims, 13 Drawing Sheets

EEG SIGNAL MONITORING ADAPTER DEVICE CONFIGURABLE ON EYEWEAR

CROSS-REFERENCE TO RELATED PATENT DOCUMENTS

This patent application claims the benefit of priority of U.S. Provisional Application No. 63/028,632 entitled "EEG (Electroencephalography) Measuring Adapter for Eyewears," filed 22 May 2020, which is hereby incorporated herein by reference in its entirety.

FIELD OF THE INVENTION

The present application generally relates to devices for monitoring, detecting, and processing electroencephalogram (EEG) signals of the human brain. More specifically, the present invention discloses an instant and discrete EEG monitoring device or adapter that can be used with eyewear.

BACKGROUND

Generally speaking, EEG is a monitoring method that records the electrical activity of the brain. EEG measures the brainwaves noninvasively via electrodes/sensors placed on the scalp and helps to establish an accurate diagnosis of brain activity. In neurology, one of the common diagnostic applications of EEG is in diagnosing epilepsy. For patients with epilepsy, it is crucial, for medical professionals, to detect the unusual electrical activity in the brain when a seizure is triggered. When the patients do not experience a seizure the brain activity may remain normal. This means unless the patients experience a seizure during EEG recording, the doctor cannot diagnose the type of seizure in full confidence. Due to the unpredictable occurrence of seizures and the limited consulting duration per patient, e.g. a session of EEG in hospital, there is indeed an urgent need for a portable, invisible, and wearable EEG device that can be continuously worn by the patients throughout the day to overcome the current constraints of laboratory-based or hospital-based EEG tests.

Likewise, EEG monitoring also facilitates to optimize the efficiency of medical treatment of mental disorders, Parkinson's disease, and Alzheimer's disease. Several studies show that EEG signals can be used to determine the mental status, emotions, and moods of a user, and it has been applied to diagnose the mental disorders of patients. The detection of emotional profile via EEG signals is particularly important as it reflects the symptoms of mental disorders in the early stage and can be used to derive the patient's mood pattern (i.e. mood tracking), tracking the efficacy of the designated treatment accurately. In addition, the patient's emotional triggers can be found and further resolved with the professional's help to improve the life quality of the patient. At the moment, mood tracking is done manually by the patient to log at fixed time slots. It often lacks accuracy as it relies on memories to recall the moods throughout a day. Furthermore, the act of recalling negative feelings may aggravate the mental status of the patient. The application of EEG monitoring can resolve these inconveniences by providing automatic mood tracking. To achieve mood tracking for a long duration throughout the day, having an invisible EEG monitoring device is essential for the field of mental health.

Alzheimer's disease (AD) is a neurodegenerative disorder that is characterized by cognitive deficits that result in the reduced capacity of patients in daily life and behavioral disturbances. EEG has been demonstrated as a reliable tool in the research of AD and the diagnosis as it contributes to the differential diagnosis and the prognosis of the disease progression. Additionally, such recordings of EEG can add important information related to drug effectiveness. Similarly, EEG has been proven to be necessary for efficiently managing Parkinson's disease. A portable and invisible EEG device can facilitate the monitoring of these diseases without causing additional disturbances in daily life.

For all of these diseases and many more, effective monitoring of brain activities via EEG for a long duration is essential. This is because certain health information such as the occurrence of emotional triggers and other abnormalities of electrical activity in the brain does not only take place exclusively in hospitals, in laboratories, or in private, but anytime, anywhere. Various systems for monitoring EEG have been known for several years and with the general technological development, EEG monitoring systems, which may be worn continuously by a person to be monitored, have been devised. However, most of the existing prior art EEG devices have bulky and obvious structures that can be worn exclusively in laboratories or in private.

In the existing prior arts, several efforts have been made to provide EEG monitoring device with one or more electrodes integrated as a part of eyewear, for example, U.S. Pat. No. 9,016,857B2, US20160054569, CN103976733A, CN103690161A, and so on. The main issues with such systems are the EEG monitoring device and its sensors/electrodes are built in a specific piece of eyewear that just has one fixed structural configuration for all users. In such EEG systems embedded in eyewear, it is a fact that eyewear cannot be easily replaced by users due to the configured EEG monitoring device or sensors therein. The fixed structure of eyewear limits the adjustment to the individual user's head size so these existing EEG monitoring devices fail in fitting on the user comfortably. Consequently, these systems have issues such as discomfort during the use and poor quality of EEG signals. Furthermore, eyewear nowadays is not only considered as a tool, but also a fashion accessory. Imposing EEG-embedded eyewear with fixed appearances can limit the user's acceptance and further degrade the user's engagement with EEG monitoring.

In order to overcome these aforementioned issues, the inventor herein proposes a device in the form of an eyewear adapter that can be attached or configured on any existing eyewear without changing the overall look of the eyewear. The removable design of the proposed eyewear adapter gives users the freedom to mount it over different eyewear to optimize the user's engagement with, and adherence to, EEG monitoring.

SUMMARY

It is an objective of the present invention to provide an EEG monitoring device or adapter that can be removable and configured on eyewear.

Another objective of the present invention is to provide an eyewear adapter device that can be easily configured or integrated with eyewear and act as an invisible design without compromising the original looks of the eyewear.

Another objective of the present invention is to provide an EEG adapter for eyewear that ensures the user's maximum comfort and is capable of ensuring stable EEG signal acquisition. The proposed EEG adapter for eyewear is configurable onto the frames of eyewear, specifically onto the temples of the eyewear. The application of EEG dry electrodes makes this proposed eyewear adapter easy to use without extra preparation and suitable for all kinds of users.

The proposed eyewear adapter is an invisible design, assuring instant, invisible, and stable EEG monitoring throughout daily life.

Another objective of the present invention is to provide an EEG adapter that is not only capable of measuring EEG signals of the human brain but is also capable of measuring electrooculogram (EOG) to provide more comprehensive information such as emotional recognition.

These and other features and advantages of the present invention will become apparent from the detailed description below, in light of the accompanying drawings.

BRIEF DESCRIPTION OF ACCOMPANYING DRAWINGS

The novel features of the present invention, as to its structure, organization, use, and method of operation, together with further objectives and advantages thereof, will be better understood from the following drawings in which various examples will be presented. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION

Figure 1:
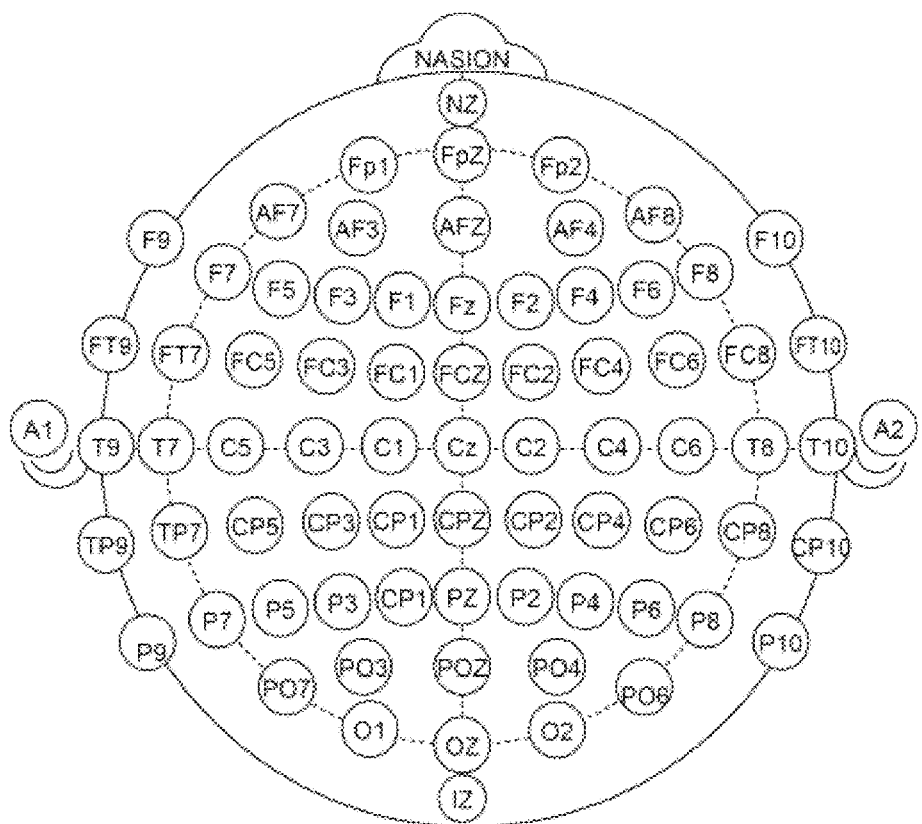
FIG. 1 is a diagram that illustrates a 10-10 system internationally recognized and that allows EEG electrode placement to be standardized for effective EEG monitoring.

As used in the specification and claims, the singular forms "a", "an" and "the" may also include plural references. For example, the term "an article" may include a plurality of articles. Those with ordinary skill in the art will appreciate that the elements in the figures are illustrated for simplicity and clarity and are not necessarily drawn to scale. For example, the dimensions of some of the elements in the figures may be exaggerated, relative to other elements, in order to improve the understanding of the present invention. There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be understood that the present invention utilizes a combination of components as a result of an instant and invisible EEG monitoring device or adapter that can be used on top of eyewear. Accordingly, the components have been represented to show only specific and pertinent details for an understanding of the present invention, so as not to obscure the disclosure with details which will be readily apparent to those with ordinary skills in the art having the benefit of the description herein. As required, detailed embodiments of the present invention are disclosed herein; however, it should be understood that the disclosed embodiments are merely exemplary of the present invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Furthermore, the terms and phrases used herein are not intended to be limiting but rather to provide an understandable description of the present invention.

References to "one embodiment", "an embodiment", "another embodiment", "one example", "an example", "another example", and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment. The words "comprising", "having", "containing", and "including", and other forms thereof, are intended to be equivalent in meaning and be open-ended so that an item or items following any one of these words is not meant to be an exhaustive listing of such an item or items or meant to be limited to only the listed item or items. Unless stated otherwise, terms such as "first" and "second" are used to arbitrarily distinguish between the elements or entities. Thus, these terms are not necessarily intended to indicate temporal or other prioritization of such elements or priorities.

The eyewear adapter of the present invention will be described with reference to the accompanying drawings, which should be regarded as merely illustrative without restricting the scope and ambit of the present invention. The proposed eyewear adapter facilitates EEG monitoring in users or patients in a more continuous and simpler fashion. One can use the removable adapter upon eyewear to conduct EEG measurements continuously and invisibly in daily life and receive the measurement result which can be further shared with medical professionals.

Figure 2:
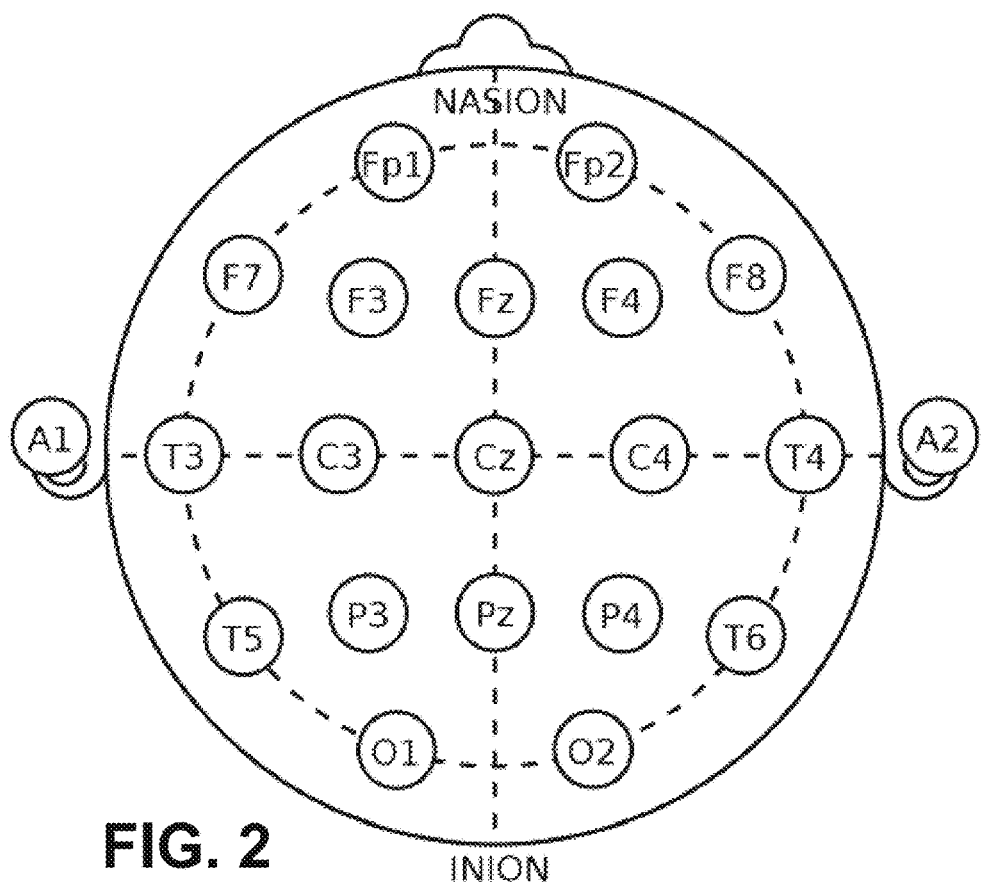
FIG. 2 is a diagram that illustrates a conventional 10-20 system.

FIG. 1 is a diagram that illustrates a 10-10 system which is internationally recognized and ensures the placement of EEG electrodes to be standardized for further analysis. The 10-10 system of FIG. 1 is derived by modifying the conventional 10-20 system (as shown in FIG. 2) and is referred to as Modified Combinatorial Nomenclature (MCN). As illustrated in FIG. 2, the conventional system divides the scalp into 10% or 20% of the total front-back or right-left distance of the skull, and therefore the electrode spacing is proportional to the skull. EEG electrodes are placed to cover all the brain regions which are broadly categorized as Frontal (F), Temporal (T), Parietal (P), and Occipital (O). The numbering system is odd numbers to the left side and even numbers to the right side, while z represents midline numbers. The 10-10 system shown in FIG. 1 uses 1, 3, 5, 7, 9 for the left hemisphere which represents 10%, 20%, 30%, 40%, 50% of the inion-to-nasion distance, respectively. Compared to the 10-20 system of FIG. 2, in the 10-10 system of FIG. 1, the new letter codes are applied. The introduction of extra letter codes allows the naming of intermediate electrode sites, namely: AF—between Fp and F, FC—between F and C, FT—between F and T, CP—between C and P, TP—between T and P, and PO—between P and O, Also, the 10-10 system renames four electrodes of the 10-20 system: T3 becomes T7, T4 becomes T8, T5 becomes P7, and T6 becomes P8.

Figure 3:
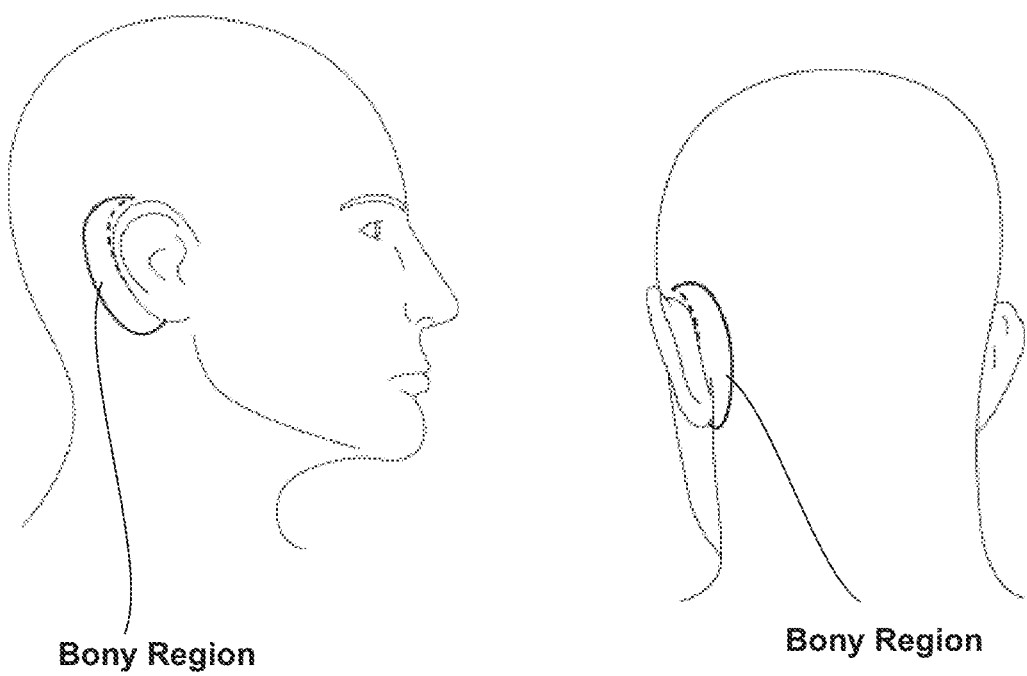
FIG. 3 is a diagram that illustrates a bony region behind the ears for the placement of the reference electrode(s) for effective EEG monitoring.

FIG. 3 is a diagram that illustrates a bony region behind the ears and can be used for the placement of reference electrode(s) according to various embodiments of the present invention.

Figure 4:
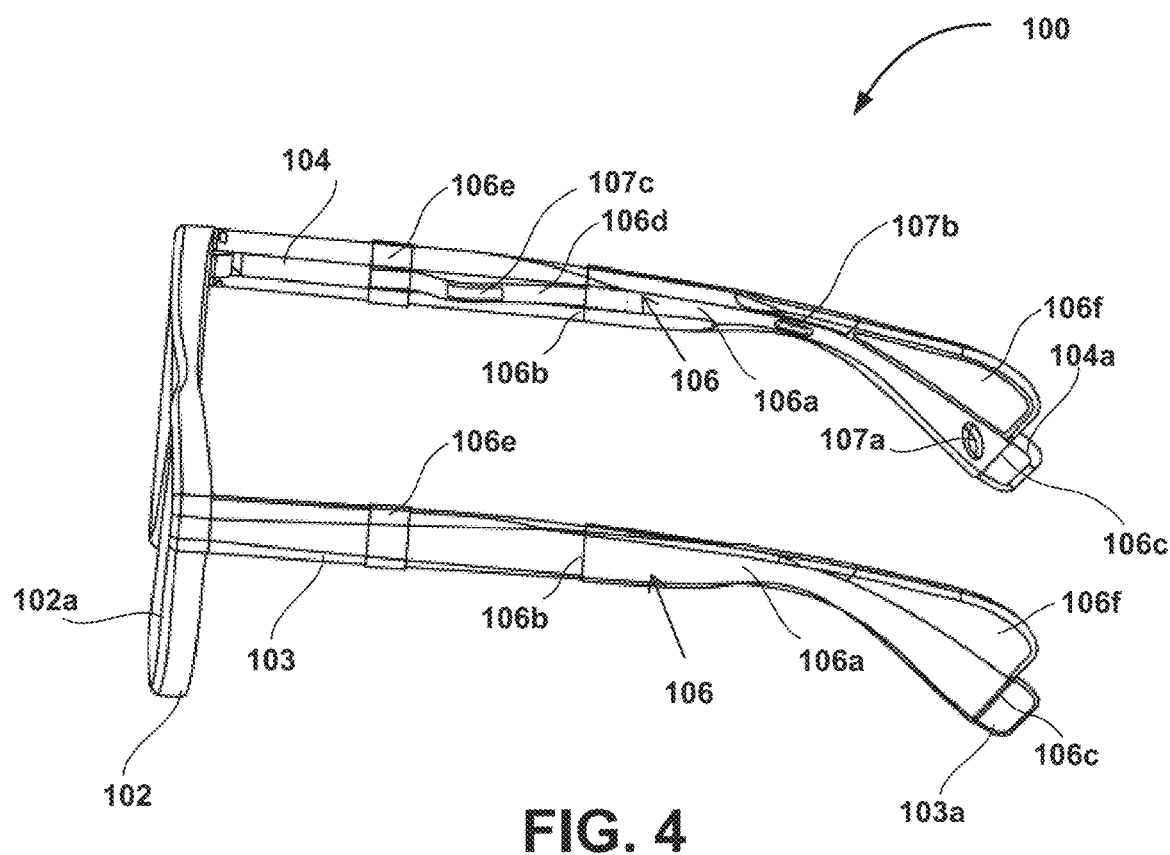
FIG. 4 shows an eyewear adapter device mounted on eyewear, according to an embodiment of the present invention.

FIG. 4 shows an eyewear adapter device mounted on eyewear, according to an embodiment of the present invention. As seen, the eyewear 100 like any conventional eyewear or glasses include a frame structure 102 for holding the eye lenses 102a, a left arm 103, and a right arm 104 where both arms are commonly referred to as temples, configured to rest over the user's ears when wearing eyewear 100. The two temples 103, 104 of the eyewear 100 are normally connected to the frame 102 at one end by hinges. These two temples also include temple tips/earpieces 103a, 104a at the other end.

The eyewear adapter 106 of the present invention includes a main body 106a configured in the form of a sleeve so that the intended temples of the eyewear 100 (i.e. the left temple 103 or right temple 104) can be inserted by sliding inside the main body of the adapter 106a. The main body 106a may include one open aperture/opening or two open apertures/openings 106b, 106c at both ends as shown. In another embodiment, the main body 106a may just include an opening or aperture at one end and be closed at the other end. In such case, only the opening 106b is present and the temple tips 103a, 104a of the eyewear 100 may not be visible but covered by the main body 106a. Furthermore, the main body 106a is preferably configured in a length of less than half of the temple 103, 104 of the eyewear 100. However, this should not be construed as a limitation. Additionally, the main body 106a is made of elastic materials including but not limited to silicone and Thermoplastic Polyurethane (TPU) and has an adequate width of the openings so that every eyewear 100 can easily adapt to this main body 106a by sliding it over the temples 103, 104. At the same time, this combination of material properties and the adequate width of opening also assures a tight fit and the fixed position of the main body 106a over eyewear 100 during use.

The eyewear adapter 106 further includes a ring 106e which is made of similar material as that of the main body 106a. The ring 106e is sized to fit over the temple of the eyewear 100 and can be slid over the temple 103, 104 of the eyewear 100 along the hinged end of the temple 103, 104 and the main body 106a. In some other embodiment, the ring 106e may be configured in the form of a semicircular hook instead of a circular ring.

The eyewear adapter 106 further includes a strip 106d which is configured to connect the main body 106a and the ring 106e. The strip 106d further embodies an EEG electrode 107c. The combination of the ring 106e and the strip 106d allows the user to place the EEG electrode 107c accurately at the locations FT9/FT10 of the 10-10 system (FT9/FT10 positions can be located from FIG. 1, which is usually the temple area of the user's skull) by simply sliding the ring 106e toward either the hinged end of the temple 103, 104 or the main body 106a using the fingers. Besides, the combination of the ring 106e, the strip 106d, and the elongated shape of EEG electrode 107c also allows the adjustment of the protruding structure of the stripe to optimize the contact pressure between the skin and the electrode 107c. This location of the electrode 107c on FT9/FT10 can also acquire the EOG signal that can be used for further interpretations such as facial expression of emotion recognition. The strip 106d may be made of a material including but not limited to Polyimide (PI) and Polyethylene terephthalate (PET)

In addition to the EEG electrode 107c, the main body 106a embodies an EEG electrode 107a that is located at the rear part of the eyewear adapter 106, for example near the temple tip 103a, 104a of the eyewear 100 as shown in FIG. 4. In another embodiment, the EEG electrode 107c is located on the housing 106f. The EEG electrode 107a may be positioned in the vicinity of the bony region behind the user's ears as shown in FIG. 3 such as the positions A1 and A2 (mastoid points in FIG. 1). The main body 106a embodies another EEG electrode 107b accurately positioned at T9/T10 position of the 10-10 system (as seen in FIG. 1). Besides, the adapter 106 may equip additional electrode(s) for EEG or EOG signal acquisition, e.g. an electrode as the bias input of the electronics unit. The EEG eyewear adapter 106 of the present invention uses dry electrodes which are made of materials including but not limited to conductive polymer, non-skin-irritating metal, conductive ink, and conductive-resistant hydrogel. This application of EEG dry electrodes, requiring no extra preparation, facilitates the use of EEG measurement for all users.

The main body 106a of the eyewear adapter 106 further includes a portion or housing 106f that houses an electronics unit (not seen) therein in a concealed manner. In some embodiments, the housing 106f may also be positioned at the lower end of the temple tip 103a, 104a, and embody the electronics unit therein.

Figure 5:
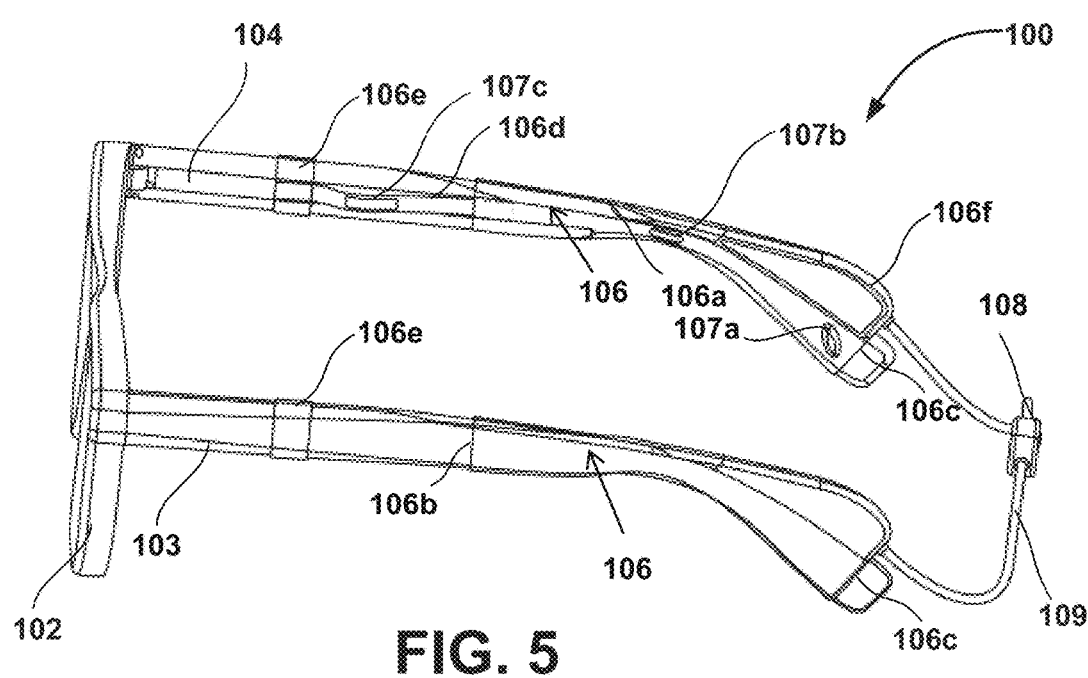
FIG. 5 shows an eyewear adapter device mounted on eyewear, according to another embodiment of the present invention.

Referring to FIG. 5 shows an eyewear adapter device mounted on eyewear, according to another embodiment of the present invention. The embodiment shown in FIG. 5 is essentially identical to the embodiment of the eyewear adapter 106 shown in FIG. 4 and thus lots of identical components and parts of the eyewear adapter 106 are not repeatedly described here in order to keep the description more concise. The main difference that can be noted in FIG. 5 is the location of the electronics unit 108, which instead of being located in a concealed manner inside the housing 106*f* (as in FIG. 4) is separately located outside. The electronics unit 108 is electrically connected to EEG electrodes 107*a*-107*c* and optionally any other additional electrode(s) of the eyewear adapter 106 using an electrical cable 109. It should be understood by those skilled that the eyewear adapter 106 may be designed to have more EEG electrodes without limitation to three EEG electrodes.

Figure 16:
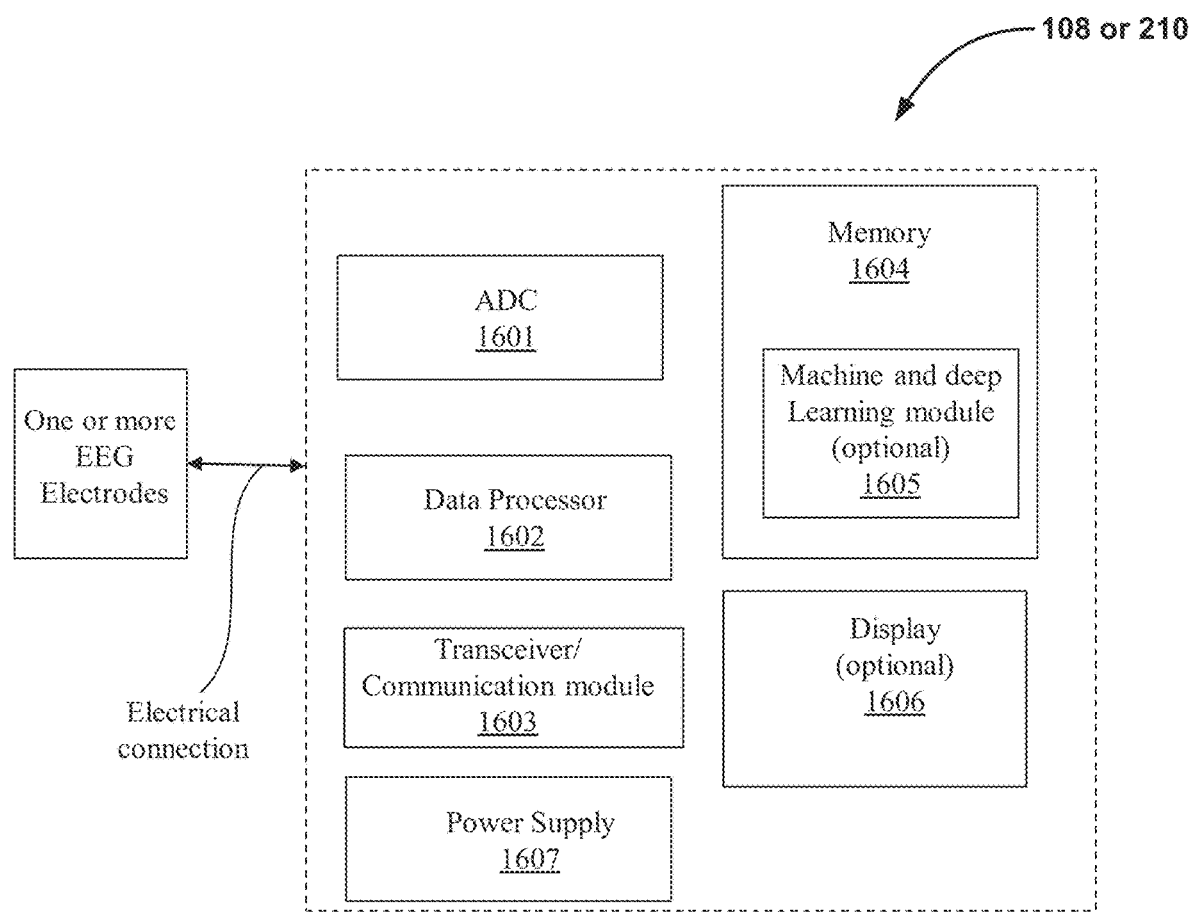
FIG. 16 is an exemplary block diagram that shows an electronics unit used for processing the EEG signals acquired by EEG electrodes.

The electronics unit preferably include an analog-to-digital converter (ADC) 1601, a data processor 1602, a transceiver/communication module 1603, a memory 1604, a machine and deep learning module 1605 embedded or stored in the memory 1604, a display 1606, and a power supply 1607 as shown in a general block diagram in FIG. 16.

Figure 17:
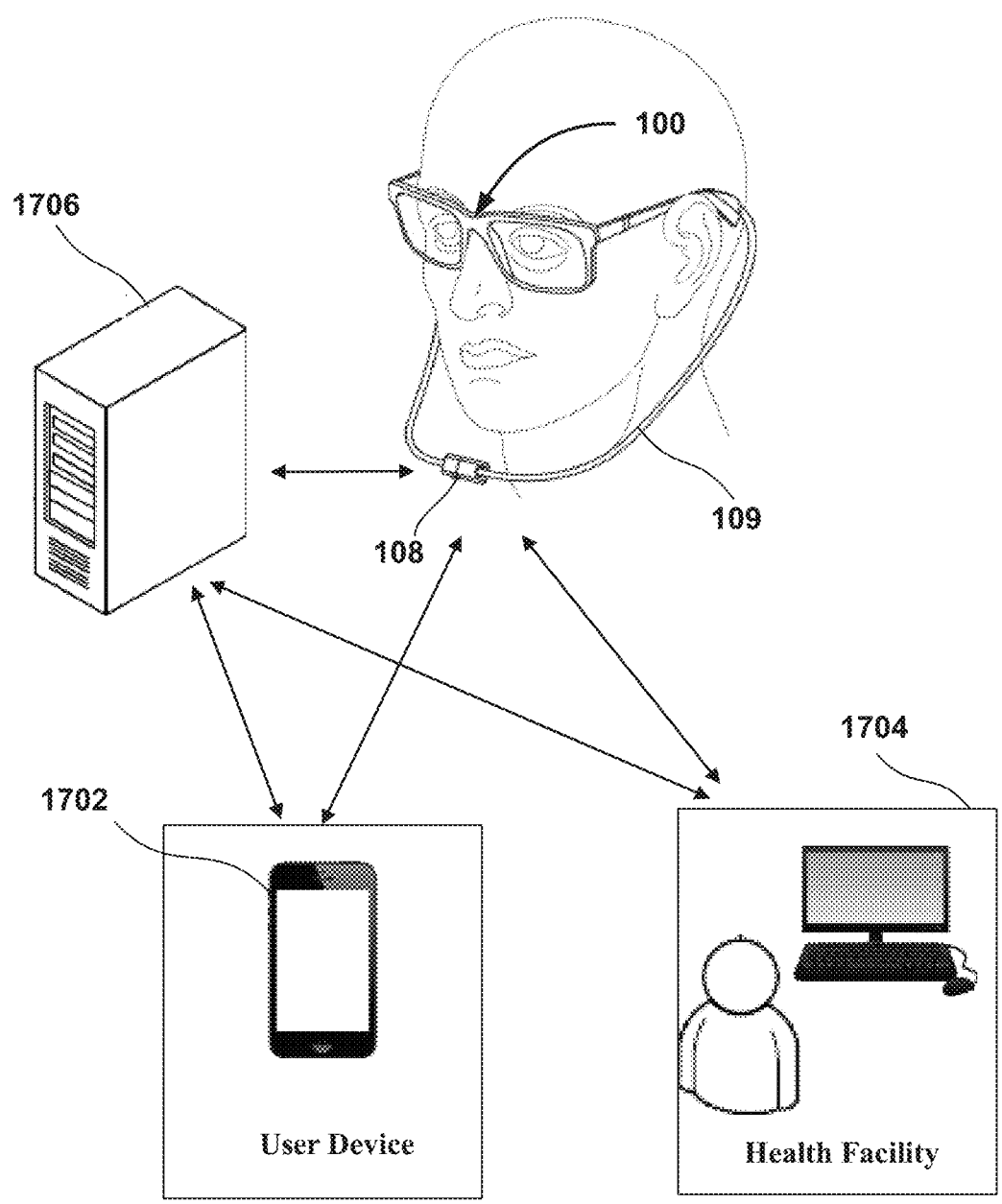
FIG. 17 is an exemplary environmental diagram that shows the communication between the electronics unit of the EEG adapter mounted on the eyewear and the mobile communication device and/or medical facility.

In operation, the EEG electrodes 107*a*-107*c* configured on the eyewear adapter 106 acquire EEG signals from the user's brain at any instant of time. Once the EEG signals have been measured by one or more EEG electrodes 107*a*-107*c*, the captured EEG signals in the analog form are transmitted to ADC 1601 of the electronics unit. ADC 1601 converts analog EEG signals from the user to a digital form which is then communicated to the data processor 1602. The data processor 1602 includes one or more processors/microcontrollers known in the art and conducts signal analysis. This signal analysis by the processor 1602 is powered by machine learning or deep learning algorithms 1605 that may be optionally stored in the memory unit 1604 to distinguish if the captured signal by the EEG electrodes 107*a*-107*c* is within the acceptable EEG domain (e.g. frequency, amplitude). The machine learning or deep learning algorithms 1605 can be updated regularly via wired connection or via wireless communication. After the analysis is done by the processor 1602, the result is then displayed on the display unit 1606 if a display is present in the electronics unit or transmitted via the transceiver/communication module 1603 to a user's device 1702 such as mobile phones or tablets for display as shown in FIG. 17. The EEG data from the electronics unit is preferably transmitted using wireless technologies including but not limited to WiFi and Bluetooth. The power supply 1607 is adapted to power the various components of the electronics unit.

The pre-processed EEG data shown to the user/patient on one's mobile device 1702 reminds the user to adjust the EEG eyewear adapter 106 on the eyewear 100 properly if the acquired EEG signal quality is not ideal. According to the embodiments of the present invention, the EEG data acquisition by the EEG electrodes 107*a*-107*c* will get initiated using either the user's mobile device 1702 or operating directly the electronics unit of EEG eyewear adapter 106. Additionally, the user's mobile device may be enabled to generate corresponding EEG data in various formats (.csv, .mat, .xlxs, etc.) to facilitate communication with medical professionals. The EEG analysis can be processed inside the EEG eyewear adapter 106 (by the processor 1602 of the electronics unit), the user's device 1702, or remotely on a computational cloud server 1706 via wireless communication. The server 1706 is preferably a high-end computing environment that includes all necessary components such as a storage unit, communication modules, processors, and so on. The technical details on the server 1706 are intentionally omitted in this disclosure as the server is well known in the art. The EEG data is then transferred to the mobile device 1702 to display the information to the user or the remote health facilities 1704, with the user's agreement for the purpose of patient monitoring, for further analysis or communication of health advice as shown in FIG. 17.

Figure 18A:
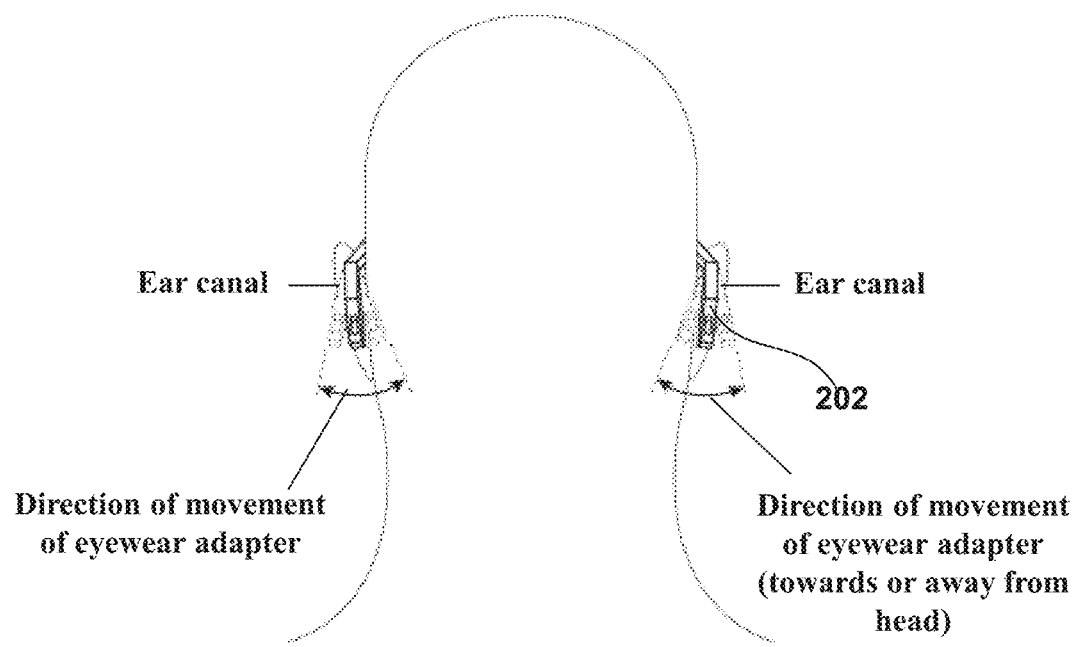
FIGS. 18A-18B are diagrams that demonstrate the possible adjustment of the eyewear adapter device mounted on the eyewear, according to an embodiment of the present invention.
Figure 18B:
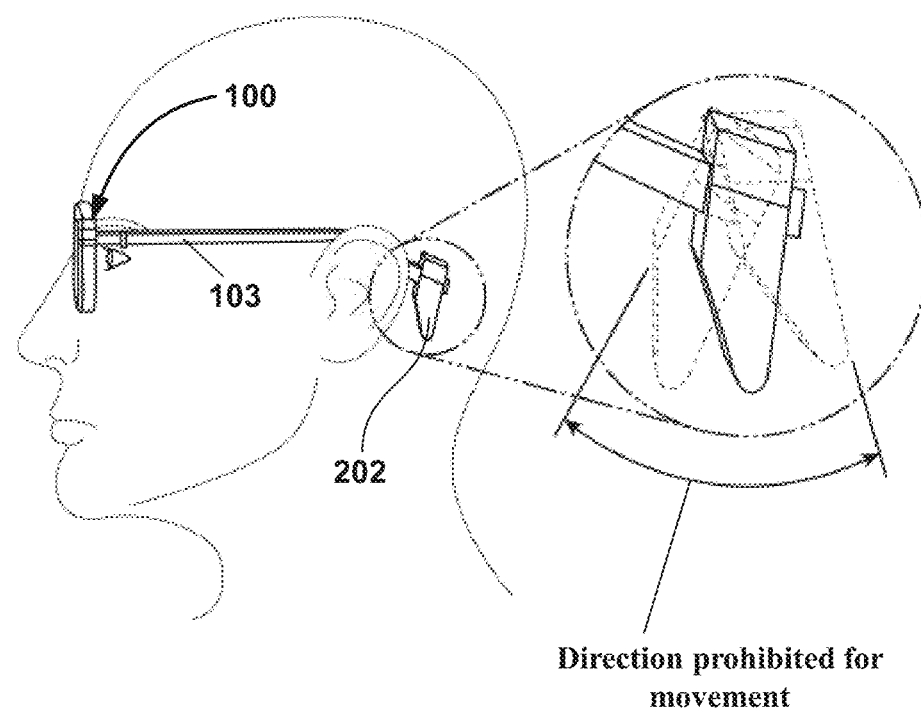
Figure 18C:
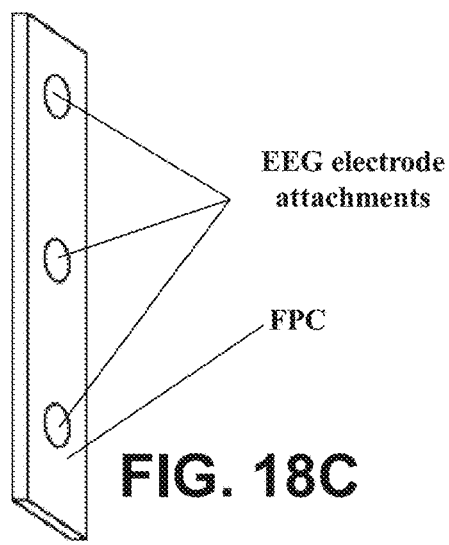
FIGS. 18C-18E show a general material organization of the proposed eyewear adapter.
Figure 18D:
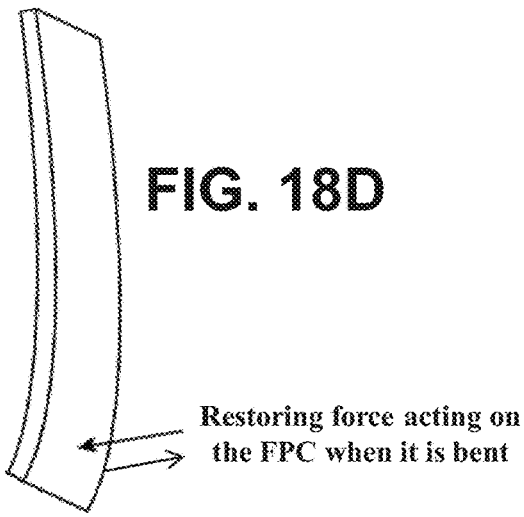
Figure 18E:
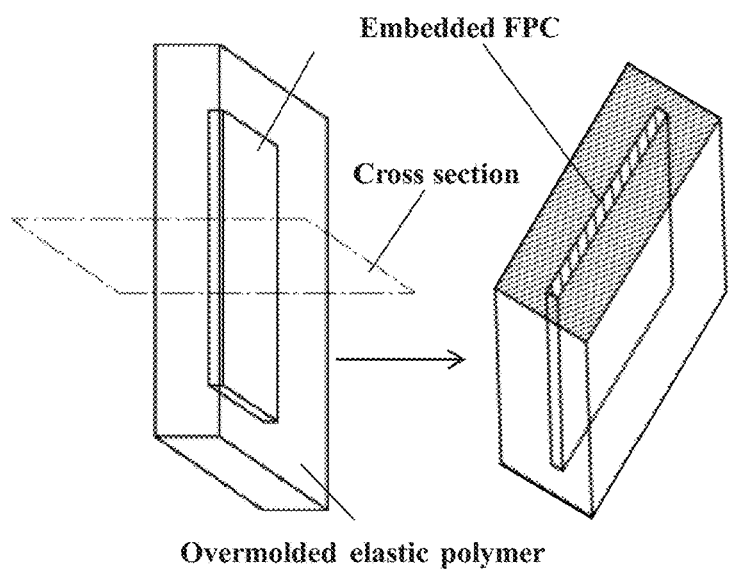

As the essence of the proposed invention and as best viewed in FIGS. 18A-18E, the EEG adapter (the main body 106*a*, the ring 106*e*, the housing 106*f*, and so on) is made mainly of soft and elastic polymer(s) including but not limited to silicone and TPU instead of rigid materials. The electrical connectivity between EEG electrodes 107*a*-107*c* may be carried out by a flexible printed circuit (FPC) which allows direct electrode attachment (as seen in FIG. 18C) to ensure a minimum thickness/dimension of the eyewear adapter 106. Besides, the FPC also works as the framework of the adapter 106 to maintain the overall shape. The FPC may be made of including but not limited to PI and PET. During the manufacturing process of the proposed EEG adapter, the FPC with the electrode(s) attached will be overmolded (using injection molding, compression molding, or similar molding processes) using the elastic polymer mentioned before (see FIG. 18E). Due to the physical properties of FPC, i.e. in the form of a sheet and with high restoring force (as seen in FIG. 18D), after overmolding, the FPC permits movement and flexibility to the eyewear adapter 106 exclusively in the direction perpendicular to the FPC's sheetlike surface plane, that is, in the frontal plane of the user, as indicated by the double-headed arrow in the embodiment displayed in FIG. 18A and not in the direction, that is, in the sagittal/longitudinal plane of the user, as indicated by the double-headed arrow in the embodiment displayed in FIG. 18B. In the eyewear adapter 106, the FPC's sheetlike surface plane faces toward the user's head, and therefore its movement toward or against the user's head is allowed, while the movement toward or away from the ear canal is prohibited. With these physical properties of FPC, the adapter 106 can be adjusted for better contact of the EEG electrode 107*a* located in the movable regions at the rear part of the eyewear adapter 106 such as the housing 106*f*, in terms of signal quality and comfort by adapting to the head size of the user. This design ensures that the EEG electrode(s), including but not limited to 107*a*, at the bony region behind the ears especially at the mastoid positions A1/A2 in FIG. 1 can be well in contact to obtain the most desirable EEG signal quality. Furthermore, the high restoring force of FPC is also advantageous to assure an adequate contact pressure of the EEG electrode 107*c* on the temple of the skull FT9/FT10, with the protruding structure created by adjusting the ring 106*e* toward the main body 106*a*. The material proposed for EEG eyewear adapter also enables regular cleaning simply by using water to sustain the hygiene without damaging the functionality of the adapter.

Figure 6:
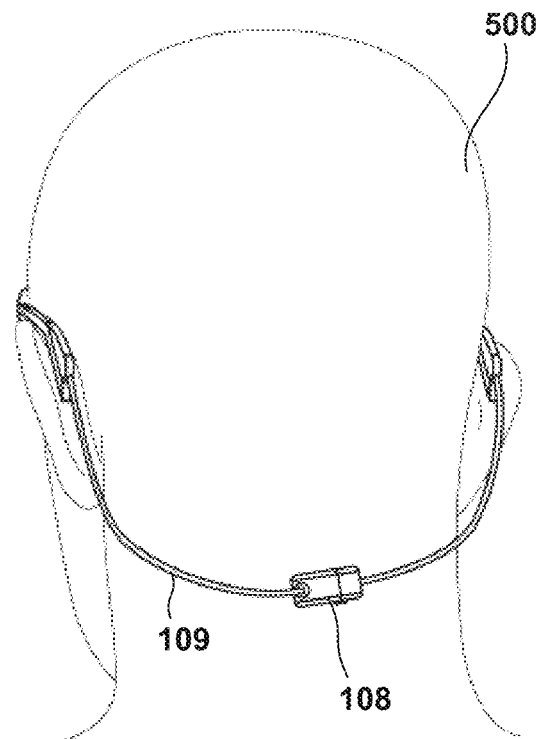
FIGS. 6-7 show exemplary use case scenarios for eyewear embodying the eyewear adapter of FIG. 5.
Figure 7:
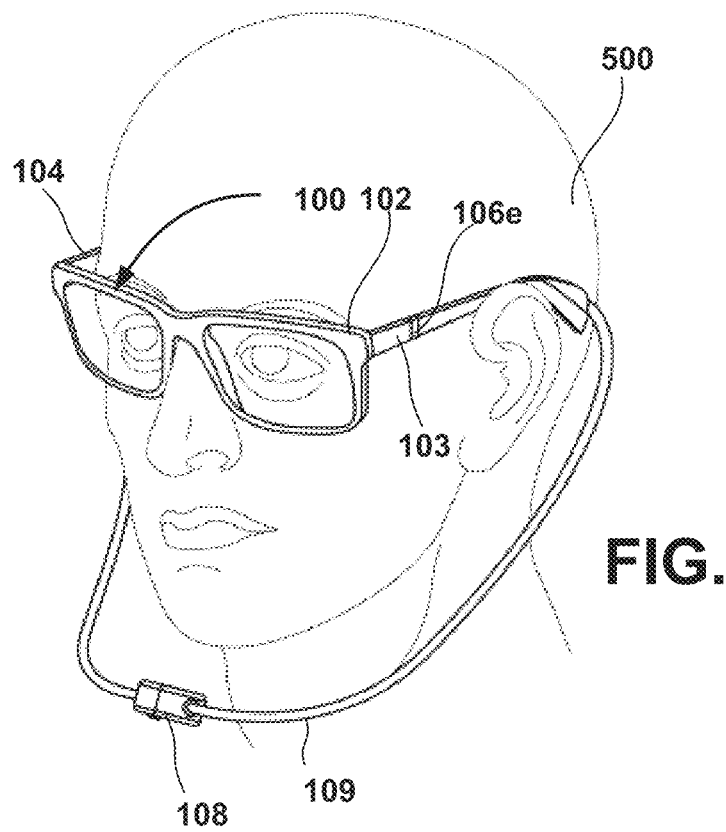

Referring to FIGS. 6 and 7, exemplary use case scenarios for the eyewear embodying the eyewear adapter of FIG. 5 are shown. As seen, the eyewear adapter 106 is mounted or worn over each of the two temples 103, 104 of the eyewear 100. When the eyewear 100 embodying the adapter 106 is worn by the user 500, the electronics unit 108 can either be located behind the neck of the user (as shown in FIG. 6) or in front beneath the chin area as shown in FIG. 7. Depending upon the length of the electrical cable 109 used to connect the electronics unit 108 and the adapter's EEG electrodes, the electrical cable 109 can work as a glasses cord when preferably positioned behind the neck of the user, and the electronics unit 108 can also be aesthetically located in the form of a pendant in the front of the user 500 preferably near the user's chest region. Once the eyewear 100 with the adapter 106 is worn by the user 500, the electrodes 107*b* is positioned at T9/T10 whereas the position for the EEG electrode 107c can be adjusted by the user 500 by sliding the ring 106e and the contact of the EEG electrode 107a can be optimized by a tilt of the movable region such as the housing 106f carrying the EEG electrode 107a until the adapter 106 receives adequate EEG signals.

Figure 8:
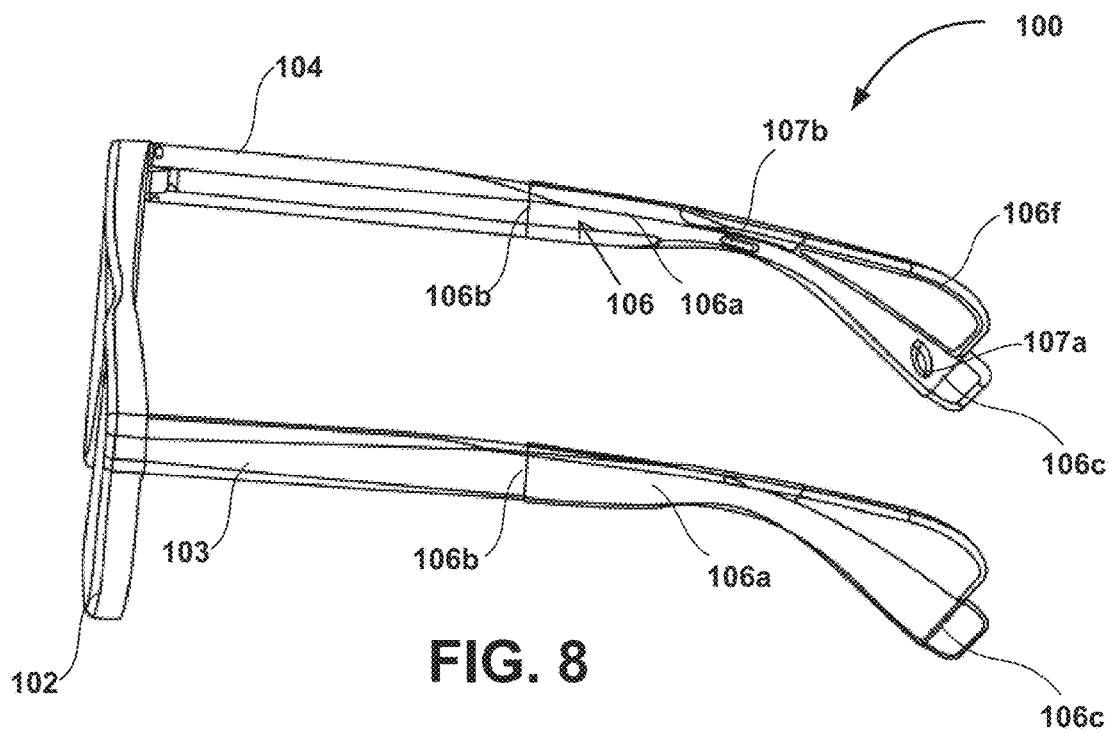
FIG. 8 shows an eyewear adapter device mounted on eyewear, according to another embodiment of the present invention.

Referring to FIG. 8, an eyewear adapter device mounted on eyewear, according to another embodiment of the present invention is shown. The embodiment shown in FIG. 8 is essentially identical to the embodiment of the eyewear adapter 106 shown and described with respect to FIG. 4 and thus lots of identical components and parts of the eyewear adapter 106 are not repeatedly described here to keep the description more concise. The main difference that can be noted in FIG. 8 is the absence of the EEG electrode 107c, the ring 106e, and the strip 106d. This embodiment of the eyewear adapter 106 includes the EEG electrodes 107a-107b. The functionality of these electrodes 107a and 107b, the electronics unit, and the configuration of the adapter's main body 106a remain identical to the design described with respect to FIG. 4.

Figure 9:
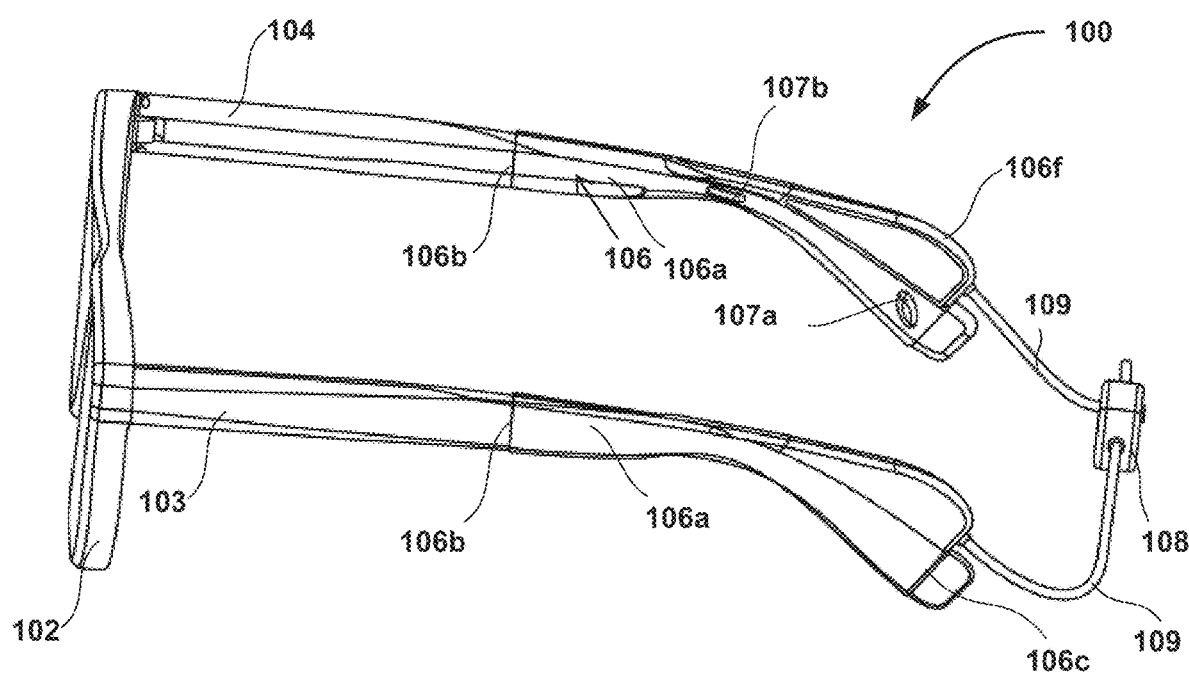
FIG. 9 shows an eyewear adapter device mounted on eyewear, according to another embodiment of the present invention.

Referring to FIG. 9 shows an eyewear adapter device mounted on eyewear, according to another embodiment of the present invention. The embodiment shown in FIG. 9 is essentially identical to the embodiment of the eyewear adapter 106 shown and described with respect to FIG. 8 and thus lots of identical components and parts of the eyewear adapter 106 is not repeatedly described here to keep the description more concise. The main difference that can be noted in FIG. 9 with respect to FIG. 8 is the location of the electronics unit 108, which instead of being located in a concealed manner inside the housing 106f (as in FIG. 8) is separately located outside. The electronics unit 108 is electrically connected to EEG electrodes 107a, 107b, and optionally additional electrode(s) of the adapter 106 using the electrical cable 109.

Figure 10:
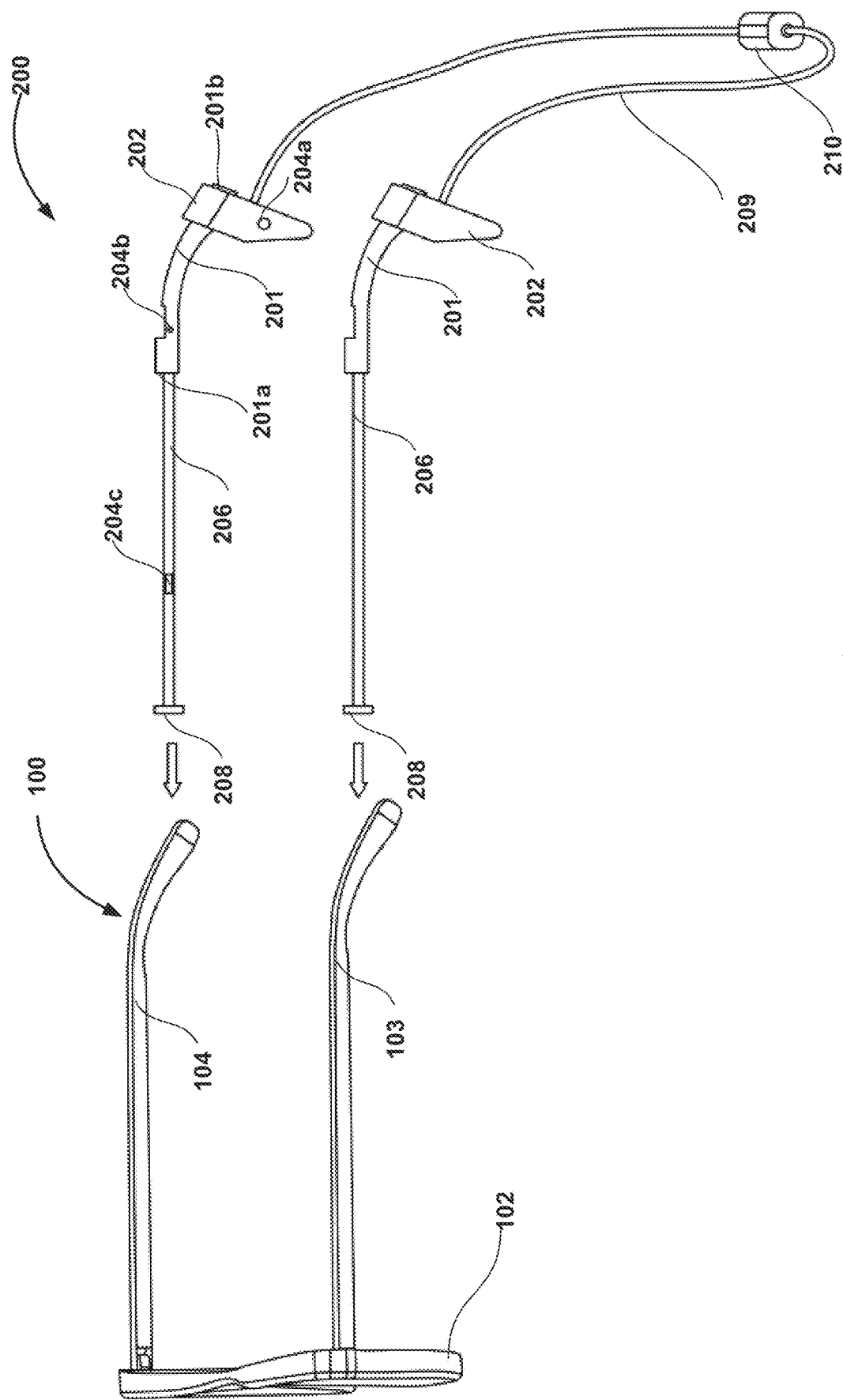
FIG. 10 is an exploded view showing eyewear and an eyewear adapter according to another embodiment of the present invention.

Referring to FIG. 10, an exploded view shows eyewear and an eyewear adapter according to another embodiment of the present invention. The eyewear adapter 200 is preferably made using the same constructional technique described above with respect to FIG. 18. In this embodiment, the eyewear adapter 200 includes a main body 201 similar to the main body 106a of FIGS. 4 and 5, the main body 201 acts as a sleeve for the eyewear temples 103, 104 by sliding through the openings of 201a and 201b, where 201b is positioned before the temple tip of 103, 104. The main body 201 has specifically a FPC embedded which acts as a substrate for the attachment of the EEG electrode 204b. The EEG electrode 204b is similar to the EEG electrode 107b measuring EEG signals at the positions T9/T10 of the 10-10 system (see FIG. 1). At one end of the main body 201 close to the temple tip of 103, 104, a curved earpiece 202 is located and is configured as an extension extending out of the main body 201. This curved earpiece 202 is flexible and its flexibility comes from the combination of the internal FPC and the overmold elastic polymer upon the FPC. This design organization ensures movement of the curved earpiece 202 in the direction toward or against the user's head (i.e. in the frontal plane of the user) and prevents movement of the curved earpiece 202 in the direction toward or away from the ear canal (i.e. in the sagittal plane of the user), ensuring the positioning of the EEG electrode 204a (located at the curved earpiece 202), the same positions as the EEG electrode 107a in FIGS. 4-5, in the vicinity of the bony region (as indicated in FIGS. 18A and 18B) when the eyewear adapter 200 is in use. Further, as seen, the eyewear adapter 200 includes a strip 206 that embodies an EEG electrode 204c and connects to the main body 201 at one end. The strip 206 is operationally constructed and positioned similar to the strip 106d described above. The EEG electrode 204c measures EEG signals at the positions of FT9/FT10 of the 10-10 system (see FIG. 1) as 107c in FIGS. 4-5. The eyewear adapter 200 also includes a slidable ring 208 operationally constructed and positioned similar to the ring 106e described above with reference to FIG. 4. The eyewear adapter 200 (a pair in fact, one for the left and one for the right side) fits over the temples 103, 104 of the eyewear 100 when in use. Additionally, just like the electronics unit 108 shown in FIG. 5, an electronics unit 210 in this embodiment is located outside of the main body 201 and electrically connected to the EEG electrodes 204a-204c using an electrical cable 209.

Figure 11:
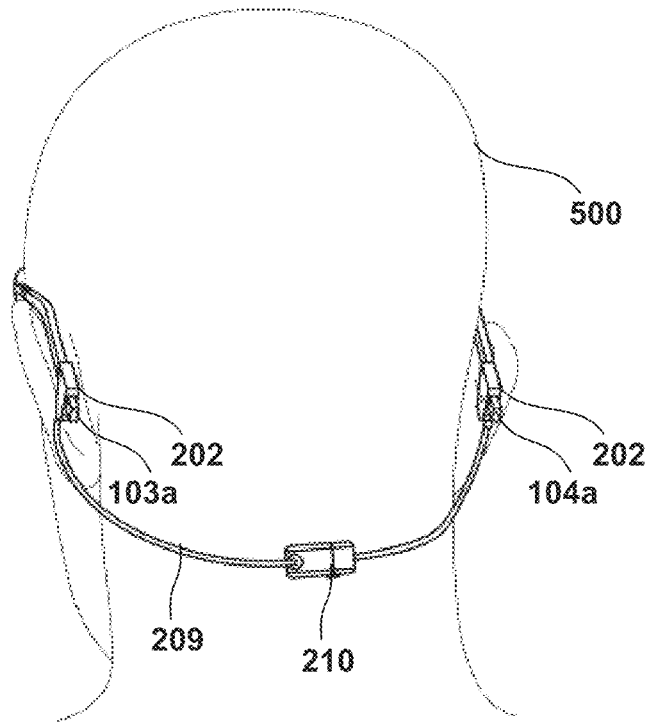
FIGS. 11-12 show exemplary use case scenarios for eyewear embodying the eyewear adapter of FIG. 10.
Figure 12:
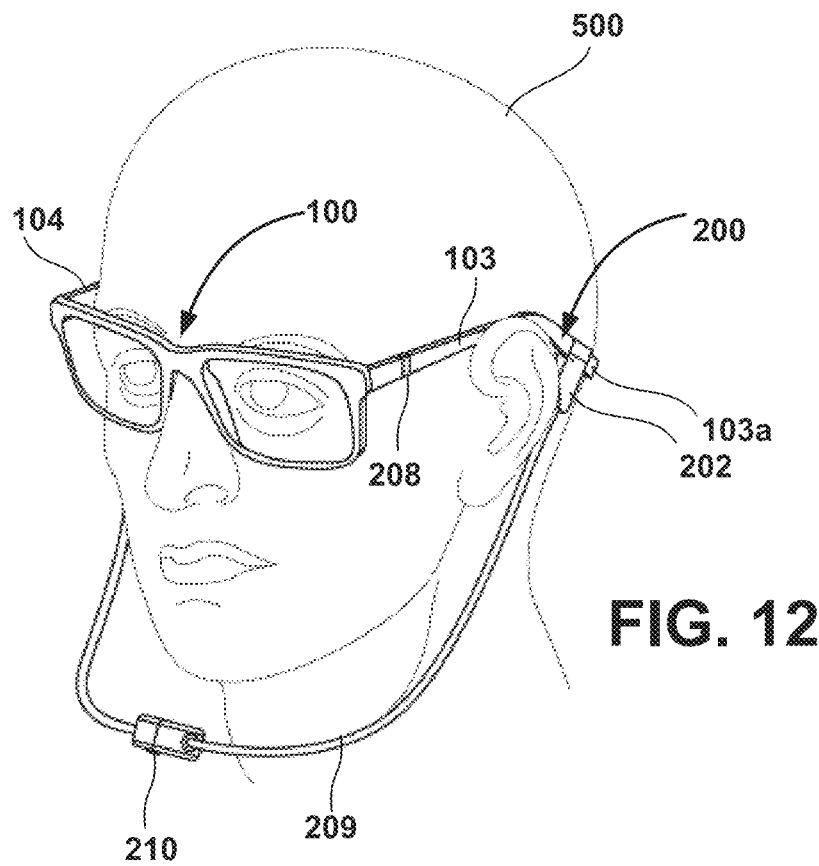

Referring to FIGS. 11 and 12, exemplary use case scenarios for the eyewear embodying the eyewear adapter of FIG. 10 are shown. As seen, the eyewear adapter 200 is mounted or worn over each of the two temples 103, 104 of the eyewear 100. When the eyewear 100 embodying the eyewear adapter 200 is worn by the user 500, the electronics unit 210 can either be located behind the neck of the user (as shown in FIG. 11) or in front beneath the chin area as shown in FIG. 12. Depending upon the length of the electrical cable 209 used to connect the electronics unit 210 and the adapter's EEG electrodes 204a-204c, the electrical cable 109 can work as a glasses cord when preferably positioned behind the neck of the user, and the electronics unit 210 can also be aesthetically located in the form of a pendant when the combination of the electronics unit 210 and the electrical cable 209 is located in front of the user 500 preferably near the user's chest region. Once the eyewear 100 with the eyewear adapter 200 is worn by the user 500, the positions of the electrodes 204a and 204c are adjustable whereas the position for the EEG electrode 204b is pretty much fixed. The position of the electrode 204a can be adjusted in the direction toward or away from the user's head by the user 500 to be located in the vicinity of the bony region (see FIG. 3) by adapting to the head size of the user with the flexible design of the curved earpiece 202. The adjustability of the EEG electrode 204c by the user 500 is done by sliding the ring 208 until the eyewear adapter 200 receives adequate EEG signals on the location FT9/FT10.

Figure 13:
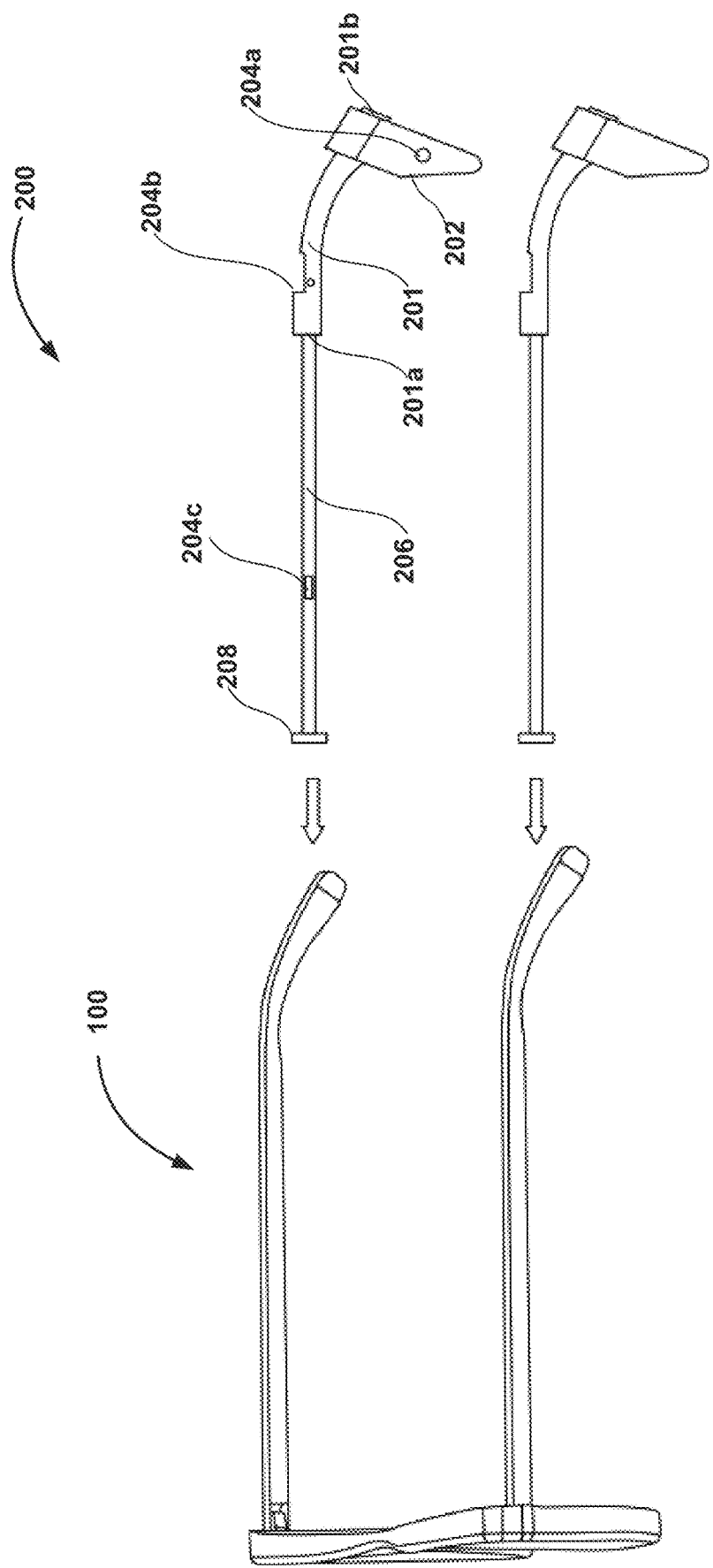
FIG. 13 is an exploded view showing eyewear and an eyewear adapter according to yet another embodiment of the present invention.

Referring to FIG. 13, an exploded view showing eyewear and an eyewear adapter according to yet another embodiment of the present invention. The eyewear adapter 200 shown in this embodiment is identical to the eyewear adapter described above with reference to FIG. 10. In contrast to the embodiment shown in FIG. 10, the design shown in FIG. 13 embodies the electronics unit (not seen) within the main body 201 or the curved earpiece 202 ensuring the electronics unit remains concealed.

Figure 14:
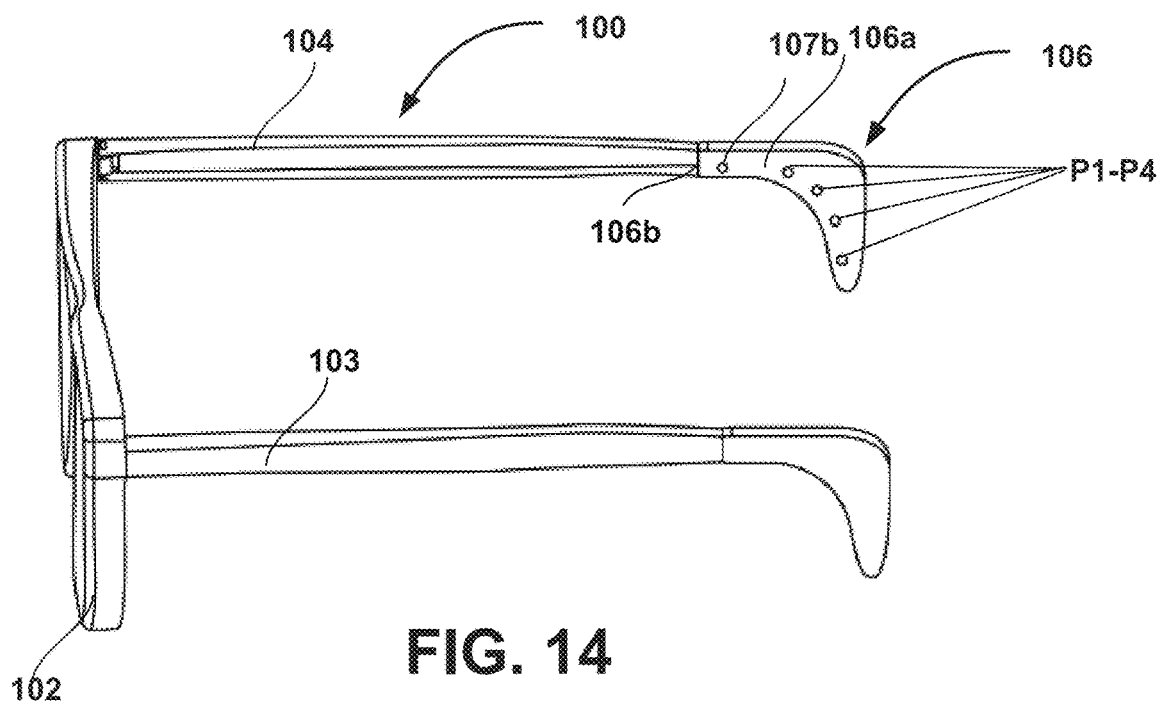
FIG. 14 shows an eyewear adapter device mounted on eyewear, according to another embodiment of the present invention.
Figure 15:
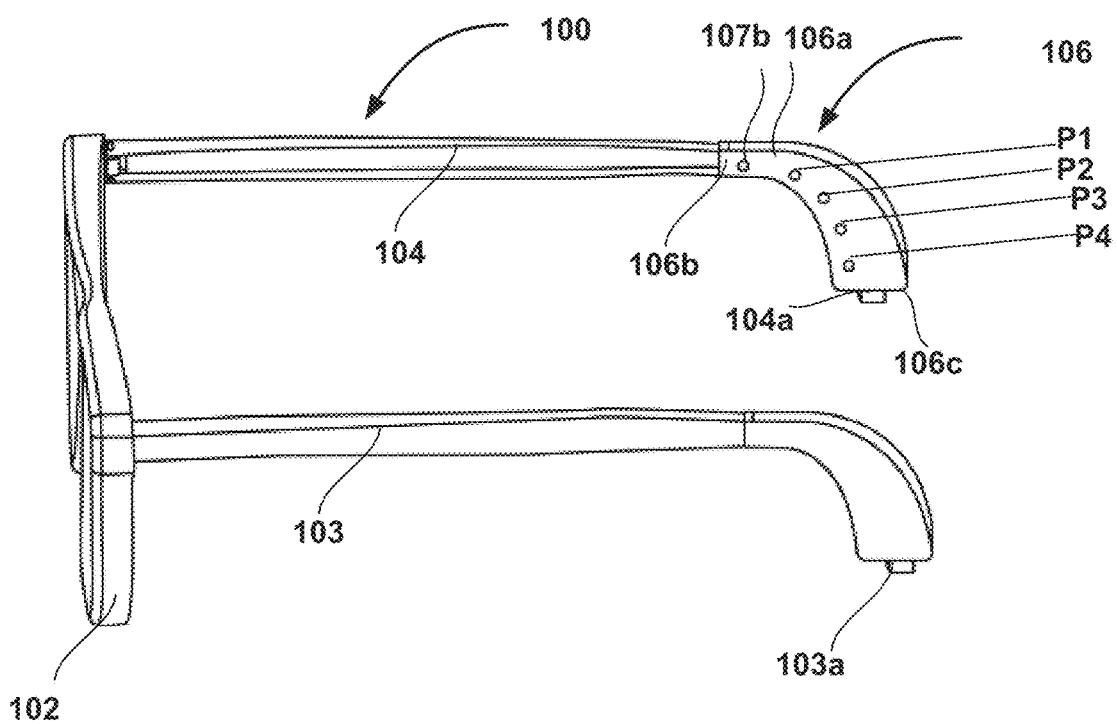
FIG. 15 shows an eyewear adapter device mounted on eyewear, according to another embodiment of the present invention.

Referring to FIGS. 14 and 15, an eyewear adapter device mounted on eyewear, according to other embodiments of the present invention are shown. FIG. 14 shows an eyewear adapter 106 mounted over the temples 103, 104 of the eyewear 100. The adapter 106 fits over the temples 103, 104 and is oriented downward along with the temple tips of the eyewear 100. The adapter 106 acts as a sleeve with one open end 106b. The temples 103, 104 of the eyewear 100 are inserted inside the adapter 106 through the opening 106b. An EEG electrode 107b is accurately positioned at T9/T10 positions (as can be located in FIG. 1). Another EEG electrode(s) may be positioned within the downward extending portion of the eyewear adapter 106 that covers the bony region behind the user's ears (as shown in FIG. 3) when the eyewear adapter 106 is worn by the user. There could be multiple points/positions for placement of the electrode including but not limited to P1, P2, P3, and P4. The eyewear adapter shown in FIG. 15 is very similar to the embodiment shown in FIG. 14; however, the adapter 106 of FIG. 15 is designed in the form of a sleeve with two open ends 106b, 106c. The adapter 106 design is such that it extends downward behind or before the temple tips 103a, 104a of the eyewear 100. The adapter 106 includes an EEG electrode 107b accurately positioned at T9/T10 positions (as can be located in FIG. 1). Another EEG electrode(s) may be positioned in an adapter portion that covers the bony region behind the ears of the user when the eyewear adapter 106 is worn by the user. There could be multiple points/positions for placement of the electrode(s) including but not limited to P1, P2, P3, and P4. The eyewear adapter 106 of FIGS. 14-15 may be formed using the same constructional technique as described above with reference to FIG. 18 to offer flexibility, ensuring optimized comfort and EEG signal quality. Although FIGS. 14-15 explicitly show the eyewear adapter 106 with one electrode 107b at T9/T10 and another electrode(s) that cover(s) the bony region behind the ears of the user (located at P1-P4 positions) which can be equivalent to the EEG electrode 107a as in FIGS. 4-5, it should be understood that this embodiment can also be implemented for three electrodes on each side by adding one adjustable electrode positioned at FT9/FT10 using the setup of the ring 106e, the strip 106d, and the EEG electrode 107c described above in FIGS. 4-5. The electronics unit is concealed inside the main body 106a for both embodiments shown in FIGS. 14-15 and it should be understood that the electronics unit can be placed outside the main body 106a with the electrical cable as the combination of 108 and 109 shown in FIGS. 5, 9, 10.

Although the description and claims appended herein focus on describing and claiming parts, components of the proposed eyewear adapter configured on one of the temples of the eyewear, as seen in the accompanying figures, it should be understood that the identical adapter's parts or components are configured over both the temples of the eyewear.

Although particular embodiments of the invention have been described in detail for purposes of illustration, various modifications and enhancements may be made without departing from the spirit and scope of the invention. The scope of the invention is accordingly defined by the following claims.

What is claimed is:

1. An eyewear adapter device (106) for eyewear (100) having a temple, comprising: a main body (106a) sized and configured in the form of a sleeve with at least one opening and configured to receive said temple (103, 104) of the eyewear (100) therein; a first EEG electrode (107c); a ring (106e) configured to fit over the temple (103, 104) of the eyewear (100), the ring (106e) is operable by a user to move the first EEG electrode (107c) of the eyewear adapter (106) device (106) toward or away from the main body (106a) to ensure the first EEG electrode (107c) is positioned at either location FT9 or FT10 of the 10-10 system of EEG electrode placement when in use; a second EEG electrode (107a) of the eyewear adapter device (106) configured to be located at a temple tip (103a, 104a) of the temple (102, 104), wherein the second EEG electrode (107a) is configured to be positioned on a bony region behind an ear of the user when in use; a third EEG electrode (107b) of the eyewear adapter device (106) positioned in the main body (106a) corresponding to either location T9 or T10 position of the 10-10 system of EEG electrode placement when in use; and an electronics unit configured to receive and process EEG-related data from the first EEG electrode (107c), the second EEG electrode (107a), and the third EEG electrode (107b).

2. The eyewear adapter device (106) of claim 1, wherein the first EEG electrode (107c) of the eyewear adapter device (106) is mounted over a strip (106d) that connects the main body (106a) and the ring (106e).

3. The eyewear adapter device (106) of claim 1, wherein the ring (106e) is slidably fitted over the temple of the eyewear (100) to facilitate adjustment of the first EEG electrode (107c) of the eyewear adapter device (106).

4. The eyewear adapter device (106) of claim 1, wherein the positioning of the first EEG electrode (107c) at either location FT9 or FT10 of the 10-10 system of EEG electrode placement further enables capturing of EOG signals that can be used for further interpretation.

5. The eyewear adapter device (106) of claim 1, wherein the first EEG electrode (107c), the second EEG electrode (107a), and the third EEG electrode (107b) are dry electrodes made of conductive polymer, non-skin-irritating metal, conductive ink, and conductive-resistant hydrogel.

6. The eyewear adapter device (106) of claim 1, wherein the electronics unit is located in a portion or housing (106) of the main body (106a) in a concealed manner.

7. The eyewear adapter device (106) of claim 1, wherein the electronics unit (108) is located externally of the main body and is electrically connected to the first EEG electrode (107c), the second EEG electrode (107a), and the third EEG electrode (107b) using an electrical cable (109).

8. The eyewear adapter device (106) of claim 1, wherein the electronics unit comprises at least one of: an analog to digital converter (1601); a power supply (1607) a data processor (1602); a transceiver/communication module (1603); a memory (1604) storing a machine or deep learning algorithm (1605); and a display (1606).

9. The eyewear adapter device (106) of claim 1, wherein the eyewear adapter device (106) comprises a flexible printed circuit (FPC) acting as an internal framework for the eyewear adapter device (106) wherein the FPC comprises a material selected from a group consisting of polyimide (PI) and polyethylene terephthalate (PET).

10. The eyewear adapter device (106) of claim 9, wherein the flexible printed circuit (FPC) comprises attachments for the first EEG electrode (107c), the second EEG electrode (107a), and the third EEG electrode (107b).

11. The eyewear adapter device (106) of claim 1, wherein the eyewear adapter device (106) comprises soft and elastic polymer overmolding around the flexible printed circuit (FPC) to provide freedom of movement to the eyewear adapter device (106) or a portion thereof in the direction toward or away from the user's head in the frontal plane and prevent movement in the direction toward or away from an ear canal of the user in the sagittal plane.

12. The eyewear adapter device (106) of claim 1, wherein when in use the second EEG electrode (107a) of the eyewear adapter device (106) is positioned at either location A1 or A2 of the 10-10 system of EEG electrode placement.

13. An eyewear adapter device (106) for eyewear (100) having a temple,
comprising: a main body (106a) sized and configured in the form of a sleeve with at least one opening and configured to slidingly receive said temple (103, 104) of the eyewear (100);
a first EEG electrode (107a) of the eyewear adapter device (106) configured to be located at a temple tip (103a, 104a) of the temple (103, 104) wherein, when in use, the eyewear adapter (106) is in use the first EEG electrode (107a) is configured to be positioned on a bony region behind an ear of the user;

a second EEG electrode (107b) of the eyewear adapter device (106) positioned in the main body (106 a) corresponding to either location T9 or T10 of the 10-10 system of EEG electrode placement when in use;

an electronics unit configured to receive and process EEG-related data from the first EEG electrode (107a) and the second EEG electrode (107b);

wherein, the eyewear adapter device (106) comprises soft and elastic polymer overmolding around a flexible printed circuit (FPC) to provide freedom of movement to the eyewear adapter device (106) or a portion thereof in a direction toward or away from the user's head in the frontal plane and prevent movement in the direction toward or away from the ear canal of the user in the sagittal plane.

14. The eyewear adapter device (106) of claim 13, wherein the eyewear adapter device (106) extends downward along with the temple tip (103a, 104a) of the eyewear (100) or extends downward behind or before the temple tip (103a, 104a) of the eyewear 100.

15. The eyewear adapter device (106) of claim 13 wherein the FPC is configured as an internal framework for the eyewear adapter device (106), and the FPC comprises a material selected from a group consisting of polyimide (PI) and polyethylene terephthalate (PET).

16. An eyewear adapter device (200) for eyewear (100) having a temple, comprising a main body (201) sized and configured in the form of a sleeve with at least one opening (201a) and configured to slidingly receive said temple (103, 104) of the eyewear (100); a curved earpiece (202) located as an extension extending out of the main body (201); a ring (208) configured to fit over the temple of the eyewear (100), the ring (208) is operable by a user to move a first EEG electrode (204c) of the eyewear adapter (200) toward or away from the main body (201) to ensure the first EEG electrode (204c) is accurately positioned at either location FT9 or FT10 of the 10-10 system of EEG electrode placement when in use; a second EEG electrode (204a) of the eyewear adapter device (200) located on the curved earpiece (202), the second EEG electrode (204a) configured to be adjustably located at various positions on a bony region behind an ear of the user when in use; a third EEG electrode (204b) of the eyewear adapter (200) positioned at either location T9 or T10 of the 10-10 system of EEG electrode placement when in use; and an electronics unit configured to receive and process EEG-related data from the first EEG electrode (204c), the second EEG electrode (204a), and the third EEG electrode (204b).

17. The eyewear adapter device (200) of claim 16, wherein the first EEG electrode (204c) of the eyewear adapter device (200) is mounted over a strip (206) that connects the main body (20) and the ring (208).

18. The eyewear adapter device (200) of claim 16, wherein the electronics unit is located in the main body (201) or the curved earpiece (202) in a concealed manner.

19. The eyewear adapter device (200) of claim 16, wherein the electronics unit (210) is located externally of the main body (201) and the curved earpiece (202) and electrically is connected to the first EEG electrode (204c), the second EEG electrode (204a), and the third EEG electrode (204b) using an electrical cable (209).

20. The eyewear adapter device (200) of claim 16, wherein the electronics unit comprises at least one of: an analog to digital converter (1601); a power supply (1607); a data processor (1602); a transceiver/communication module (603); a memory (1604) storing a machine and deep learning algorithm (1605); and a display (1606).

21. The eyewear adapter device (200) of claim 16, wherein the eyewear adapter device (200) comprises a flexible printed circuit (FPC) acting as an internal framework for the eyewear adapter device (200), and the FPC comprises a material selected from a group consisting of polyimide (PI) and polyethylene terephthalate (PET).

22. The eyewear adapter device (200) of claim 21, wherein the flexible printed circuit (FPC) comprises attachments for the first EEG electrode (204c), the second EEG electrode (204a), and the third EEG electrode (204b).

23. The eyewear adapter device (200) of claim 16, wherein the eyewear adapter device (200) comprises soft and elastic polymer overmolding around the flexible printed circuit (FPC) to provide freedom of movement to the eyewear adapter device (200) in the direction toward or away from the user's head in the frontal plane and prevent movement in the direction toward or away from the ear canal of the user in the sagittal plane.

* * * * *